United States Patent [19]

Bickert

[11] Patent Number: 5,576,541
[45] Date of Patent: Nov. 19, 1996

[54] APPARATUS FOR MEASURING THE BASIS WEIGHT

[76] Inventor: Martin Bickert, Obere Meerbach 6, D-56179 Vallendar, Germany

[21] Appl. No.: 614,218

[22] Filed: Mar. 12, 1996

[30] Foreign Application Priority Data

Mar. 17, 1995 [DE] Germany ............... 195 09 642.8

[51] Int. Cl.⁶ ............................................. G01N 23/16
[52] U.S. Cl. ........................................ 250/308; 250/358.1
[58] Field of Search ............................. 250/308, 358.1, 250/359.1, 396 ML

[56] References Cited

U.S. PATENT DOCUMENTS

| | | | |
|---|---|---|---|
| 4,194,114 | 3/1980 | Pankratov et al. | 250/308 |
| 4,678,915 | 7/1987 | Dahlquist et al. | 250/358.1 |
| 4,920,265 | 4/1990 | Chase et al. | 250/308 |

FOREIGN PATENT DOCUMENTS 1338157  11/1973  United Kingdom ............... 250/358.1

Primary Examiner—Carolyn E. Fields
Assistant Examiner—Edward J. Glick
Attorney, Agent, or Firm—Arthur A. Sapelli

[57] ABSTRACT

An apparatus for measuring the basis weight of a web-shaped material under test comprises a radioactive β radiation source on one side of the material under test and a β radiation detector on the other side of the material under test. For focusing the electrons emitted by the radioactive β radiation source, a magnetic field is provided, such that for the same source activity, significantly more β particle intensity is available on the material under test for measuring the transmission.

7 Claims, 2 Drawing Sheets

APPARATUS FOR MEASURING THE BASIS WEIGHT

BACKGROUND OF THE INVENTION

The present invention relates to an apparatus for measuring the basis weight, and more particularly, to an apparatus for measuring the basis weight of a web-shaped material under test.

U.S. Pat. No. 3,681,595 describes an arrangement of a radioactive radiation source on one side of a material under test and a radiation detector responsive to the radioactive radiation on the opposite side of the material under test for the on-line measurement of the basis weight of a web-shaped material under test. The material under test described therein is paper. As radioactive radiation sources, a β emitter (e.g., Promethium 147, Krypton 85 and Strontium 90) may be used. The radiation detector may consist of an ionization chamber or of a semiconductor detector, respectively. By measuring the transmission of the electrons emitted by the radioactive β radiation source, the basis weight of the material under test may be evaluated. In order to achieve a satisfactory signal-to-noise ratio, the radioactive radiation source must show a certain activity. On the other hand there is a desire to use a source having an activity as small as possible because of the radioactive radiation.

Also, from German patent DE-A-2800925, the measurement of the basis weight can be achieved by arranging a β radiation source and a β radiation detector side by side on the same side of the material under test and to take care by the provision of a magnetic field which extends in the plane of the material under test that the β particles emitted from the radiation source reach the radiation detector on curved trajectories. Thus, the β particles pass twice through the material under test.

The present invention improves the signal-to-noise ratio at a predetermined activity level of the radiation source. The present invention has in view a focusing of the electrons emitted by the β radiation source due to a magnetic field and due to the Lorentz force exerted by this magnetic field onto the electrons. By focusing of the emitted electrons within the lower half space in a direction versus the material under test, more β particles are available for the measuring of the transmission without changing the activity of the radiation source.

SUMMARY OF THE INVENTION

Therefore, there is provided by the present invention, an apparatus for measuring the basis weight of a web-shaped material under test, a radiation source of the apparatus having an improved signal-to-noise ratio at a predetermined activity level. The apparatus comprises a magnet arranged on a first side of the web-shaped material under test, the magnet generating a magnetic field which is essentially normal to the web-shaped material under test. A radioactive β radiation source is also arranged on the first side of the web-shaped material under test, the β radiation source being further arranged within the magnetic field. A β radiation detector is arranged on a second side of the web-shaped material under test such that β particles emitted from the β radiation source are focused on the material under test and on the β radiation detector.

Accordingly, it is an object of the present invention to provide an apparatus for measuring the basis weight of a web-shaped material under test having an improved signal-to-noise ratio at a predetermined activity of a radiation source.

This and other objects of the present invention will become more apparent when taken in conjunction with the following description and attached drawings, wherein like characters indicate like parts, and which drawings form a part of the present application.

DETAILED DESCRIPTION

Figure 1:
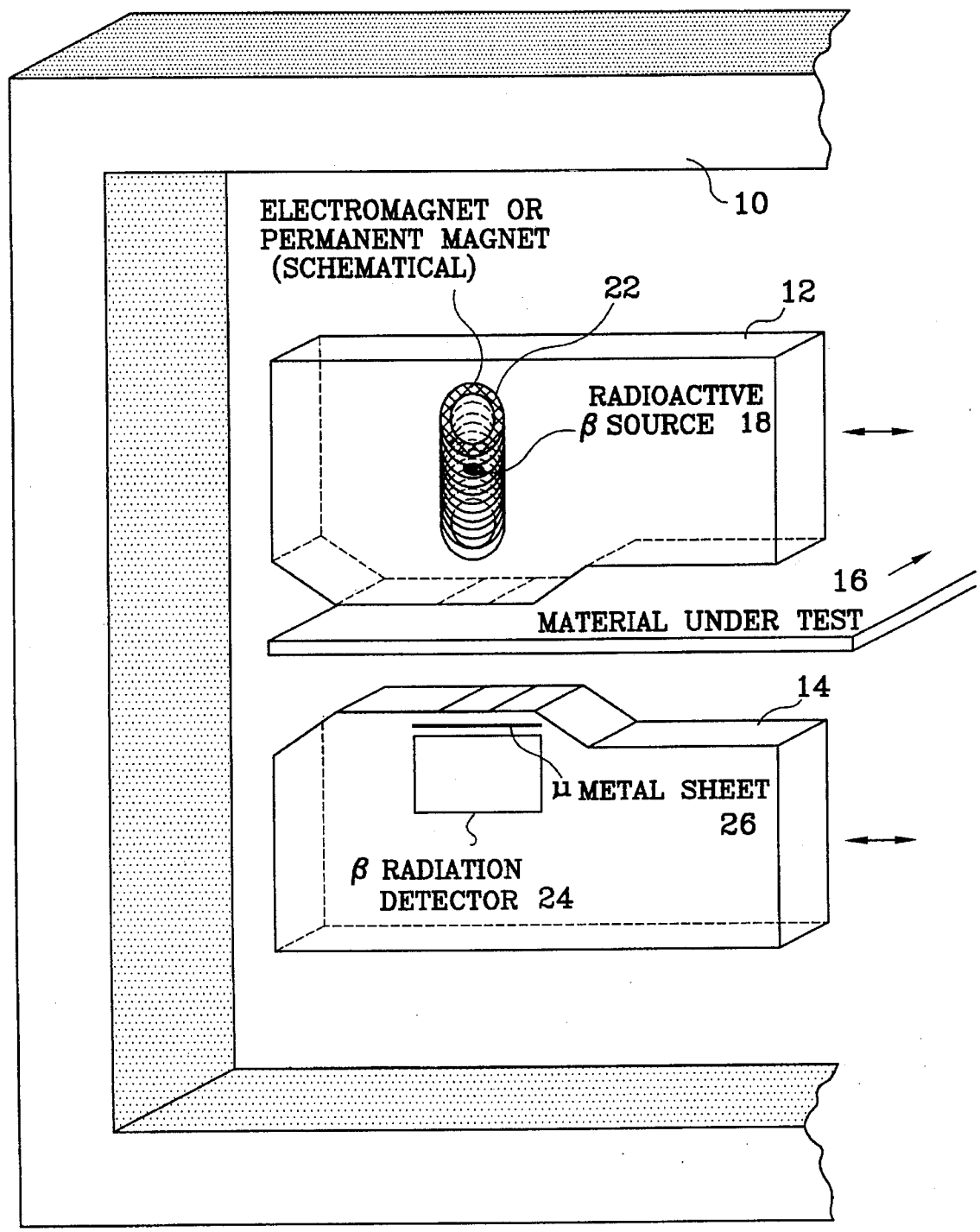
FIG. 1 shows the basic design of the inventive apparatus for measuring the basis weight.

Referring to FIG. 1, there is shown a functional diagram of the apparatus of the preferred embodiment of the present invention. An upper sensor head 12 and a lower sensor head 14, are displaceable within an O-shaped frame 10, with a material under test 16 arranged in between the upper and lower sensor hands 12, 14. (The mechanism for moving or displacing the upper and lower sensor heads 12, 14 in the direction of the arrows is well known to those skilled in the art and is not shown herein for clarity reasons.) The upper sensor heads 12 and the lower sensor head 14 are guided synchronously back and forth across the material under test 16 as shown by the double arrow, whereas the material under test is moved through the frame 10 as indicated by the direction of an arrow. The upper sensor head 12 has a radioactive β radiation source 18 which is arranged within a tube-shaped permanent magnet or electromagnet 22. Basically, any magnetic device may be used which produces a magnetic field which is essentially normal to the material under test 16 and to a radiation detector 24 included with the lower sensor head 14.

Figure 2:
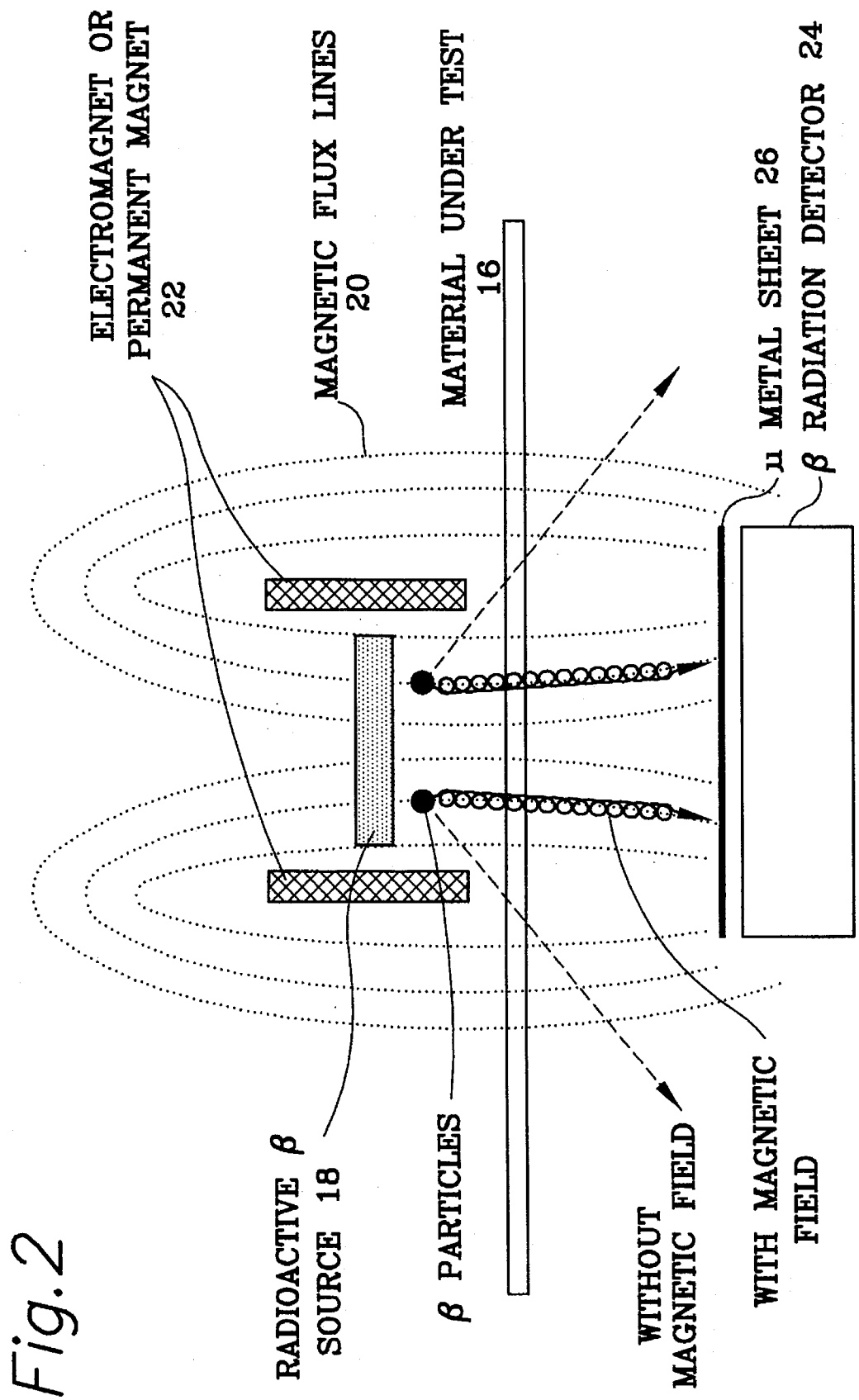
FIG. 2 shows the effect of the magnetic field on the β particles.

Referring to FIG. 2, there is diagrammatically shown the effects of a magnetic field of the electromagnet 22 on the β particles emitted from the radioactive β radiation source 18. All β particles, i.e., the electrons emitted from the radiation source 18 within the lower spheric angle <2Pi, are focused by the produced magnetic field 20 onto the material under test 16 due to the fact that the Lorentz force acts upon the electrons along the lines of the magnetic flux. Therefore, under the assumption of the same activity of the source, significantly more β particle intensity is available on the material under test 16 for measuring the transmission.

The lower sensor head 14 comprises the β radiation detector 24 which may be in a known manner an ionization chamber or a semiconductor detector, respectively. A μ metal sheet 26 is arranged on top of the radiation detector 24 in order to isolate the detection process of the β particles from the outer magnetic field.

While there has been shown what is considered the preferred embodiment of the present invention, it will be manifest that many changes and modifications can be made therein without departing from the essential spirit and scope of the present invention. It is intended, therefore, in the annexed claims to cover all such changes and modifications which fall within the true scope of the invention.

I claim:

1. An apparatus for measuring the basis weight of a web-shaped material under (16) test comprising:

a) a magnet (22), arranged on a first side of the web-shaped material under test (16) to generate a magnetic field (20) which is essentially normal to the web-shaped material under test (16);

b) a radioactive β radiation source (18) arranged on the first side of the web-shaped material under test (16), and further wherein the radioactive β radiation source (18) is arranged within the magnetic field (20); and c) a β radiation detector (24), arranged on a second side of the web-shaped material under test (16) such that β particles emitted from the radioactive β radiation source (18) are focused on the web-shaped material under test (16) and on the β radiation detector (24).

2. An apparatus according to claim 1, wherein the magnet comprises a permanent magnet.

3. An apparatus according to claim 2, wherein the permanent magnet has a tube-like shape and the radioactive β radiation source (18) is arranged within the tube-like shape.

4. An apparatus according to claim 1, wherein the magnet comprises an electromagnet.

5. An apparatus according to claim 4, wherein the electromagnet has a tube-like shape and the radioactive β radiation source (18) is arranged within the tube-like shape.

6. An apparatus according to claim 1, wherein the web-shaped material under test is paper.

7. An apparatus according to claim 1, further comprising:

a μ metal sheet (26) placed in front of the β radiation detector (24) for shielding the detector (24) against the magnetic field.

* * * * *